(12) United States Patent
Hurwitz

(10) Patent No.: US 8,501,218 B2
(45) Date of Patent: Aug. 6, 2013

(54) EDIBLE CHEW PILL JACKET

(75) Inventor: Marni Markell Hurwitz, Far Hills, NJ (US)

(73) Assignee: I Did It, Inc, Far Hills, NJ (US)

( * ) Notice: Subject to any disclaimer, the term of this patent is extended or adjusted under 35 U.S.C. 154(b) by 326 days.

(21) Appl. No.: 12/589,003

(22) Filed: Oct. 16, 2009

(65) Prior Publication Data
US 2011/0091522 A1   Apr. 21, 2011

(51) Int. Cl.
*A61K 47/00* (2006.01)
*A61K 9/68* (2006.01)
*A23K 1/16* (2006.01)

(52) U.S. Cl.
USPC ............ 424/439; 424/440; 424/442; 514/782

(58) Field of Classification Search
USPC .......................... 424/440, 442, 439; 514/782
See application file for complete search history.

(56) References Cited

U.S. PATENT DOCUMENTS

| | | | | |
|---|---|---|---|---|
| 4,329,333 A | * | 5/1982 | Barr .............................. | 424/492 |
| 4,857,333 A | * | 8/1989 | Harold ........................... | 424/442 |
| 5,296,209 A | | 3/1994 | Simone et al. .................. | 424/49 |
| 5,407,661 A | * | 4/1995 | Simone et al. .................. | 424/49 |
| 5,419,283 A | | 5/1995 | Leo ............................... | 119/709 |
| 5,792,470 A | * | 8/1998 | Baumgardner, Sr. ......... | 424/442 |
| 6,143,316 A | * | 11/2000 | Hayden et al. ................ | 424/442 |
| 6,156,355 A | * | 12/2000 | Shields et al. .................. | 426/74 |
| 6,423,357 B1 | | 7/2002 | Woods et al. .................. | 426/138 |
| 6,960,183 B2 | | 11/2005 | Nicolette ........................ | 604/57 |
| 2003/0087008 A1 | | 5/2003 | Axelrod ........................ | 426/104 |
| 2003/0093152 A1 | * | 5/2003 | Pedersen et al. ........... | 623/14.12 |
| 2004/0040869 A1 | * | 3/2004 | Menceles ........................ | 206/37 |
| 2004/0247649 A1 | * | 12/2004 | Pearce et al. .................. | 424/440 |
| 2005/0076981 A1 | * | 4/2005 | Koropitzer et al. ........... | 150/158 |
| 2008/0314333 A1 | * | 12/2008 | Hurwitz ........................ | 119/709 |

OTHER PUBLICATIONS

Feline Greenies, Pill Pockets [Downloaded Mar. 20, 2013] [Retrieved from internet <URL: http://www.1800petmeds.com/images/products/420/11029_420.jpg >], 1 page.*
Nutro, Greenies, Feline Greenies® Pill Pockets® Treats [Downloaded Mar. 20, 2013] [Retrieved from internet <URL: http://www.greenies.com/cats.aspx#/products/cat-pill-pockets >], 1 page.*
PetSmart, Customer reviews for Feline Greenies Pill Pockets, Feline Greenies Pill Pockets [Downloaded Mar. 20, 2013; comments dated Sep. 14, 2006-May 17, 2007] [Retrieved from internet <URL:http://reviews.petsmart.com/4830/2755242/greenies-feline-greenies-pill-pockets-reviews/reviews.htm?page=4 >], 4 pages.*

* cited by examiner

*Primary Examiner* — Jason M Sims
*Assistant Examiner* — Miriam A Levin
(74) *Attorney, Agent, or Firm* — Ernest D. Buff; Ernest D. Buff & Assoc, LLC; Margaret A. LaCroix, Esq.

(57) ABSTRACT

An edible chew pill jacket receives a pill/tablet or capsule that is to be administered to a pet, animal or human. The edible chew pill jacket includes a flexible top wall, side walls and bottom wall configured to form a chamber appointed to receive a pill. A flexible longitudinal slit is integrated within the top wall for providing access to the chamber for insertion of the pill within the edible chew pill jacket. The edible chew pill jacket is formulated with at least one flavoring to provide a tasty treat appointed to mask the pill's taste. The chew pill jacket substantially encapsulates the pill/tablet appointed to be orally ingested. The chew pill jacket may include medicament therein, nutrients, vitamins, or may simply be provided as a tasty treat to mask the taste of the pill.

10 Claims, 3 Drawing Sheets

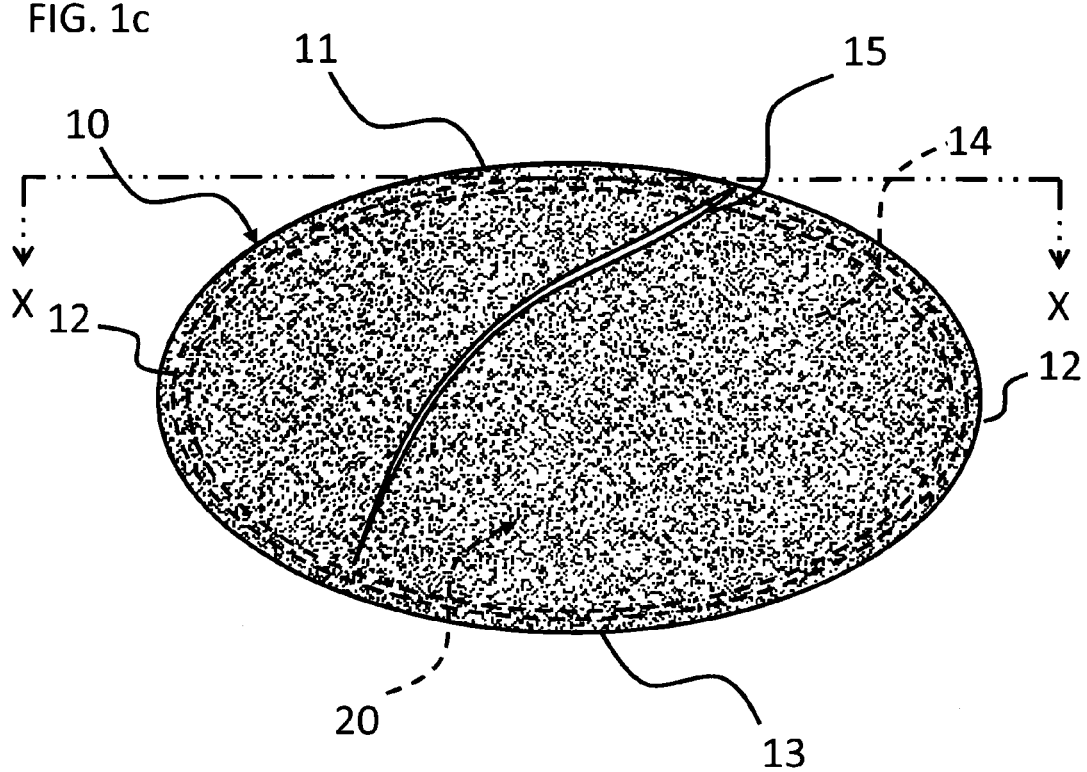

EDIBLE CHEW PILL JACKET

BACKGROUND OF THE INVENTION

1. Field of the Invention

The present invention relates to an edible chew pill jacket; and more particularly, to an edible pill jacket that is composed of flavorsome ingredients and is adapted to receive a pill to be orally ingested by an animal or person to provide an appetizing mask of the pill's taste.

2. Description of the Prior Art

Administering oral chew pill containing medications, vitamins, supplements or other active ingredients to people and pets is frequently difficult due to the undesirable taste and aftertaste of the pill. Where animals are concerned, the pill frequently is broken-up and mixed with food in order to disguise the taste of the pill. Particles of the pill are lost during the smashing or cutting process, which itself can be cumbersome, causing loss of medicament in the process. If the broken-up pill is not adequately mixed with the food, the animal will frequently simply eat around the area, causing only a very minute amount of the dosage to actually be ingested by the animal. Other methods of delivery involve delivering the pill to the animal directly into the mouth and throat. Such delivery can be difficult and requires patience and steadiness to prevent injury to either the deliverer or the animal. For example: U.S. Pat. No. 6,960,183 to Nicolette discloses a veterinary pill/capsule delivery device comprised of a dispensing head for holding a pill or capsule, the dispensing head being attached to the end of a syringe component for ejecting the pill into the animal's mouth while at the same time injecting a quantity of water into the mouth.

Delivery of chew pills to humans can also be difficult, especially where children are concerned. Certain adults and children would prefer to chew pills rather than just swallow them due to feelings of fullness in the throat or swallowing problems, however, bitter or unpleasant tastes resultant from chewing the pill are also undesirable. Currently, such individuals must either swallow the pill and suffer uncomfortable consequences, or cut-up or smash the pill and mix it with food or drink. Crushing or smashing a pill can be quite difficult, especially for the elderly, and transfer into the food or drink again results in loss of particles, interfering with dosage and delivery amounts.

In the pet arena various edible toys have been provided, however the edible toys are not constructed to house a chew pill. For example: U.S. Pat. No. 5,419,283 to Leo discloses a chew toy composed of a starch material and a polymeric material that is edible and degradable; and U.S. Pat. App. Pub. No. 20030087008 to Axelrod discloses a molded animal chew toy with a realistic appearance, and preferably made from ingredients that can be ingested by the animal. Other edible pet chew products have been provided that when chewed by a pet, function to break apart and rub against the animal's teeth to clean the teeth or provide dental care. For example: U.S. Pat. Nos. 5,296,209 and 5,407,661 to Simone et al. discloses an edible pet chew product having oral care properties. Again, these pet chew products do not include a compartment for housing and encapsulating a chew pill to be administered to the animal.

A few edible containers for administering medication to pets have been provided. For example: U.S. Pat. No. 5,792,470 to Baumgardner, Sr. discloses an edible container constructed having a length of a swaged tubular member the size of which the animal may consume and where the swaged tubular member is constructed from a tasty edible material which conceals the medication within; U.S. Pat. No. 6,143,316 to Hayden, et al. discloses a digestible pouch and method for aiding in the oral administration of medicinal agents; and U.S. Pat. No. 6,423,357 to Woods, et al. discloses an edible cup/container that can hold and contain medium and low viscosity liquids for extended periods of time. These edible containers fail to provide a cover that can simply be slipped over a pill in a substantially encapsulating manner so that a pill is nestled snuggly inside the container. Rather, each of these containers provides a bag or pouch, or tubular member, which holds a plurality of pills, power or liquid, in which the pill or medication is not snuggly fit in the container. As a result, an animal would readily eat around the portion of the container that does not come into contact with the pill. If the container is compromised and an opening is formed due to chewing, the pill or medicine would then undesirably leak out and the dosage would be lost.

Notwithstanding the efforts of prior art workers to provide various devices for delivery of pills to animals and humans, there is a need in the art for an edible chew pill jacket that can readily be slipped over a pill to substantially encapsulate it to provide a flavorful treat that masks the pill's taste. Further, there is a need in the art to provide a chew pill jacket that optionally contains a nutritional supplement therein so that ingestion of the pill jacket also provides the animal with positive health benefits.

SUMMARY OF THE INVENTION

The present invention provides a chew pill jacket for the delivery of chew pills to a pet, livestock or to a person. The chew pill jacket substantially encapsulates the pill appointed to be orally ingested by the animal. The chew pill jacket may include medicament therein, nutrients, vitamins, or may simply be provided as a tasty treat to mask the taste of the chew pill delivered orally to the recipient. A tasty treat for household pets is readily provided that discretely delivers the medicine compounded in a pill contained therein. Carob and an Arabic gum base are preferably used to bind a plurality of ingredients together to form the pill jacket. Different foods are incorporated into the carob, to provide a tasty treat for a pet, typically appealing to dogs and cats, for example. The pill jacket can also be readily adapted to include tastes desirable by children, such as sweat tastes, sour, caramels or chocolate (however, chocolate should not be utilized for pill jackets appointed to be used for canines or other pets, as chocolate is known to cause adverse reactions in dogs). The chew pill jacket can also be made with joint enhancements, such as glucosamine, and with vitamins, hormones, and the like.

The jacket houses the pill, be it medication or other, and camouflages the pill's taste. A tasty treat is thereby provided on the outside, or housing, while medication, treatment, etc. is provided on the inside. With this arrangement, the animal is more likely to favor the taste of the treat, and ingest the needed treatment without difficulty. Treat tastes may vary, as ingredients may vary. Currently utilized delivery procedures typically involve crumbling, crushing, or shredding the pill and mixing what is left into food. However, a lot of the time there is left over residue, and some of the mixture is lost, along with some of the potency. Another method currently utilized involves force feeding the pill down the throat of the animal. More often than not, this presents a struggle. Accordingly, this alternate method is frequently not very productive.

The chew pill jacket affords a pleasant taste while delivering the pill containing medication or treatment that is needed. Some people have difficulty swallowing pills. The chew pill jacket provides a more comfortable way of ingesting what is needed, and thereby remedying the situation. The base for the chew pill jacket can be carob as well, with arabic gum and a variety of ingredients added. Chocolate can be used, as well as a caramel, a healthy choice combination, or a delicious candy snack.

The chew pill jacket is comprised of an edible body having a flexible top wall, side walls and a bottom wall configured to form a chamber for receiving a pill that is to be administered to an animal or human. Preferably, the pill is a chew pill, although a pill/tablet/capsule appointed to be directly swallowed may be received in the chew pill jacket. The top wall includes a flexible longitudinal slit for providing access to the chamber for insertion of the pill/tablet/capsule within the edible body. The edible body is composed of at least one flavoring to provide a tasty treat appointed to mask the taste of the pill/tablet/capsule. Preferably, the edible body substantially encapsulates the pill/tablet/capsule in a rather snug condition so that the animal cannot readily eat just the pill jacket surrounding the pill, but will be basically forced to eat the pill along with the pill jacket. The preferred encapsulation and snug fitting condition objectively prevents the animal from eating only the pill jacket—for if the pill jacket provides too large of an interior space or chamber then the pill placed therein would move freely around, and as a result the animal could eat a portion of the pill jacket and allow the pill to fall out to consume the remainder of the pill jacket.

The chew pill jacket is appointed to be used in the delivery of a pill/tablet or capsule to an animal such as a pet dog, cat, or a horse or livestock. In another embodiment, the chew pill jacket is appointed to be used in the delivery of a pill/tablet or capsule to a human. Particularly, the chew pill jacket will provide an advantageous means to convince a child to consume a chew pill or pill to be swallowed. Or for adults and/or children who cannot swallow pill and must chew the pill for consumption.

BRIEF DESCRIPTION OF THE DRAWINGS

The invention will be more fully understood and further advantages will become apparent when reference is had to the following detailed description of the preferred embodiments of the invention and the accompanying drawings, in which:

FIG. 1c illustrates the view of FIG. 1a with the pill appointed to be administered to an animal or human received and housed within the chew pill jacket's chamber;

DETAILED DESCRIPTION OF THE INVENTION

An edible chew pill jacket is provided that is adapted to receive a pill/tablet or capsule that is to be administered to a pet, animal or human. The edible chew pill jacket includes a flexible top wall, side walls and bottom wall configured to form a chamber appointed to receive a pill. A flexible longitudinal slit is integrated within the top wall for providing access to the chamber for insertion of the pill within the edible chew pill jacket. The edible chew pill jacket is formulated with at least one flavoring to provide a tasty treat appointed to mask the pill. The chew pill jacket substantially encapsulates the pill/tablet appointed to be orally ingested. The chew pill jacket may include medicament therein, nutrients, vitamins, or may simply be provided as a tasty treat to mask the taste of the pill.

Figure 1A:
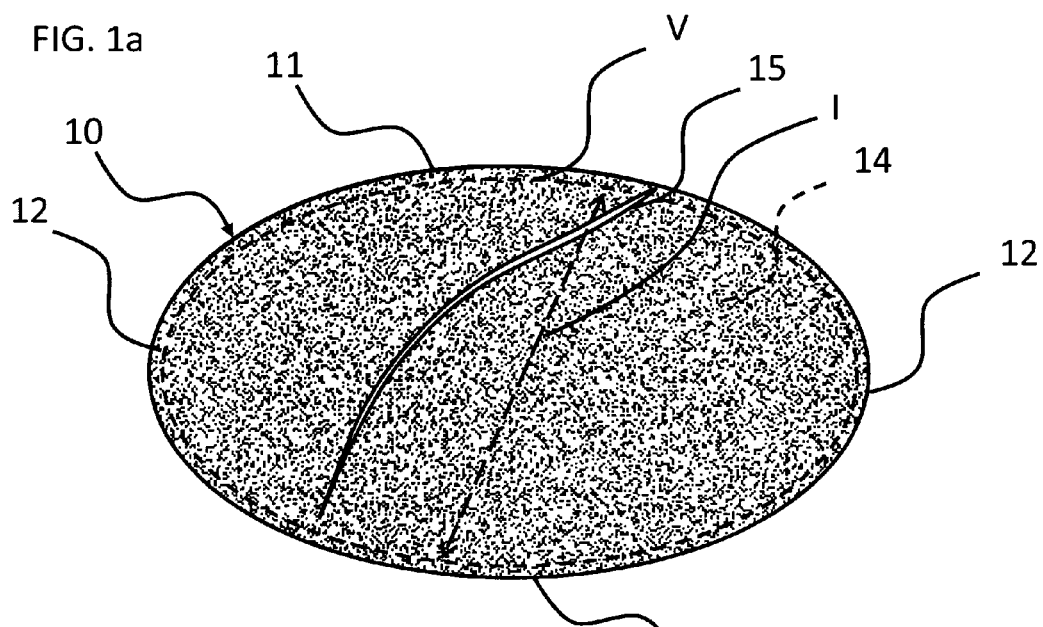
FIG. 1a illustrates a top side view of an embodiment of the edible chew pill jacket wherein the jacket is spherical in nature, showing the jacket in an empty condition as before a user places a pill within the chew pill jacket's chamber.
Figure 1B:
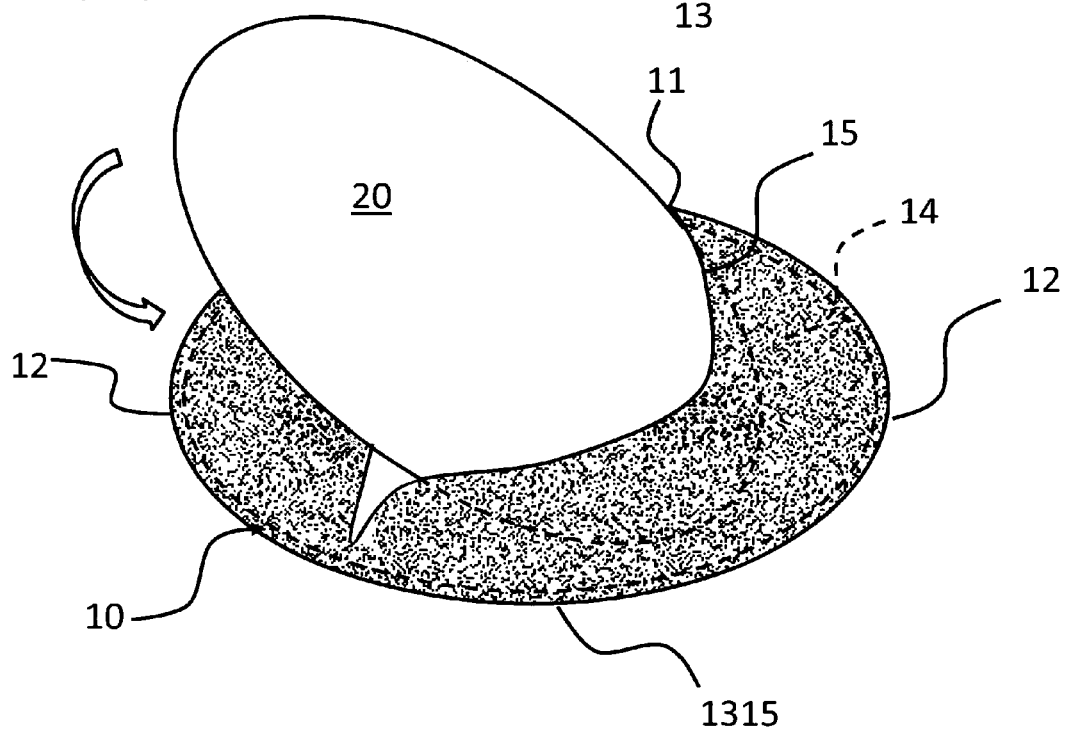
FIG. 1b illustrates the view of FIG. 1a with a pill appointed to be administered to an animal or human being inserted through the elongated slit into the chew pill jacket's chamber.

FIGS. 1a-1c illustrate top views of an embodiment of the edible chew pill jacket wherein the jacket is spherical in nature and a pill that is ready to be administered to an animal or human is inserted into the chew pill jacket for tasty consumption. Specifically, FIG. 1a illustrates the jacket in an empty condition before a user places a pill within the chew pill jacket's chamber; FIG. 1b illustrates the view of FIG. 1a with a pill being inserted through the elongated slit into the chew pill jacket's chamber; and FIG. 1c illustrates the view of FIG. 1a with the pill received and housed within the chew pill jacket's chamber right before administration. The chew pill jacket 10 is comprised of an edible body having a flexible top wall 11, side walls 12 and a bottom wall 13 configured to form a chamber 14 for receiving a pill 20 (as shown in FIGS. 1b and 1c) that is to be administered to an animal or human.

Preferably, the pill 20 is a chew pill, although a pill/tablet/capsule appointed to be directly swallowed may be received in the chew pill jacket, having applications for individuals who have difficulty swallowing pills. The top wall 11 includes a flexible longitudinal slit 15 for providing access to the chamber 14 for insertion of the pill/tablet/capsule 20 within the chew pill jacket 10. The edible chew pill jacket 10 is composed of at least one flavoring to provide a tasty treat appointed to mask the taste of the pill/tablet/capsule 20. Top wall 11, side walls 12 and bottom wall 13 are preferably of uniform thickness V. Thickness V of the walls, 11, 12 and 13, may be adjusted while either keeping the diameter I of the chamber 14 constant, or the chamber 14 diameter I may decrease with increasing wall, 11, 12 and 13, thickness V. Preferably the walls, 11, 12 and 13, have a thickness V ranging from 0.127 cm (0.05 inches) to 0.762 cm (0.3 inches). The greater the thickness V the more capable the chew pill jacket is at masking the taste of pill 20 as the ratio to the chew pill jacket to pill 20 is greater as the pill 20 and visa via jacket 10 are being chewed.

Preferably, the chew pill jacket 10 substantially encapsulates the pill 20 in a rather snug condition so that the animal cannot readily eat just the chew pill jacket 10 surrounding the pill 20. The preferred encapsulation and snug fitting condition objectively prevents the animal from eating only the pill jacket 10—for if the pill jacket 10 provides too large of an interior space or chamber 14 then the pill 20 placed therein would move freely around, and as a result the animal could eat a portion of the edible pill jacket 10 and allow the pill 20 to fall out only to consume the remainder of the pill jacket 10.

The chew pill jacket 10 is preferably provided to house only a single pill 20. However, if the pill 20 is smaller than the jacket 10 more than one pill 20 may be shoved into the jacket 10. As shown in FIGS. 1a-1c, the chew pill jacket 10 may include a textured outer surface for stimulating gums of an animal during chewing or to mask the texture of the pill 20 as it is being chewed. To accommodate most round pills 20 and/or tablets, the edible pill chew jacket 10 may be provided having a spherical or round shaped edible body as shown in FIGS. 1a-1c. Sizes in which the pill chew jacket 10 are provided correlate to typical pill 20/tablet sizes in different fields, but generally range in diameter from 0.635 cm (0.25 inches) to 2.54 cm (1 inches). Different sizes of pill chew jackets 10 can be sold separately, or a mixture of sizes can be sold together and may be sold in a variety of flavors and colors to readily indicate size. Chew pill jacket 10 diameters and sizes and shapes can be configured to specifically accommodate a particular pill 20/tablet or capsule.

Composition and flavoring of the chew pill jacket 10 is dependent on the group the jacket 10 is appointed to be used for. Generally, carob may be used; and/or arabic gum base, or chew confectionary or candy. For pets, such as canines and felines, the chew pill jacket 10 is preferably composed of meat based components or flavorings, and/peanut butter flavors. Jerky, such as from beef or other meat products can be used to compose the chew pill jacket 10. In construct, the jerky is formed and shaped into the chew pill jacket, equipped with a chamber for receiving a pill or tablet and an elongated slit that allows for insertion of the pill/tablet.

At least the top wall 11 of the chew pill jacket 10 and the elongated slit constructed therein is to be composed of a flexible malleable material. With this construction, a pill 20/tablet can be inserted through the slit 15 into the chamber 14, with the elongated slit 15 substantially returning to its original position. In this position, the pill 20/tablet is substantially encapsulated within the chew pill jacket. Flexibility is imparted to the elongated slit 15 so that the slit 15 can be deformed as pill 20 (see FIG. 1b) is being inserted, and form back to substantially its original slit condition after the pill 20 is inserted (see FIG. 1c). In this manner, the animal cannot avoid eating the pill 20/tablet when consuming the chew pill jacket 10—for if a large portion of the pill 20/tablet is exposed, the animal may eat around the pill 20/tablet. Further, masking of the pill 20/tablet flavor could be compromised if a large section or portion of the pill 20/tablet is directly exposed to the animal/person's tongue. Carob and/or an Arabic gum can be used to provide a chewy, tasty pill chew jacket 10.

When appointed to be used in human consumption, preferably the chew pill jacket 10 is composed of a fruit component, having a texture much like dried fruit, or a fruit roll-up. Real fruit or synthetic ingredients or confections may be used, and the components presented to encompass a variety of flavors, such as strawberry, apple, blueberry, banana, grape and lemon. A licorice-like candy or chewy confection may be used to compose the chew pill jacket 10, which appeals to both children and adults. Chocolate and/caramel confections can also be used for human consumption. Chocolate chew pill jackets 10 are not to be used for pets, as compositions in chocolate are toxic to dogs. The chew pill jacket may be formed as a gummy chew pill jacket composed of ingredients utilized to form gummy candy treats.

The outer surface of the chew pill jacket 10 may include a plurality of gum stimulation teeth integrated therein and projecting therefrom or an otherwise textured surface. As the animal chews on the chew pill jacket 10 with a pill 20 housed therein, the gum stimulation massage the gums increasing blood flow thereto for gum maintenance. The gum stimulation teeth may cover only a segment of the outer surface of the chew pill jacket 10, or may substantially cover the entire outer surface of the chew pill jacket 10.

Figure 2A:
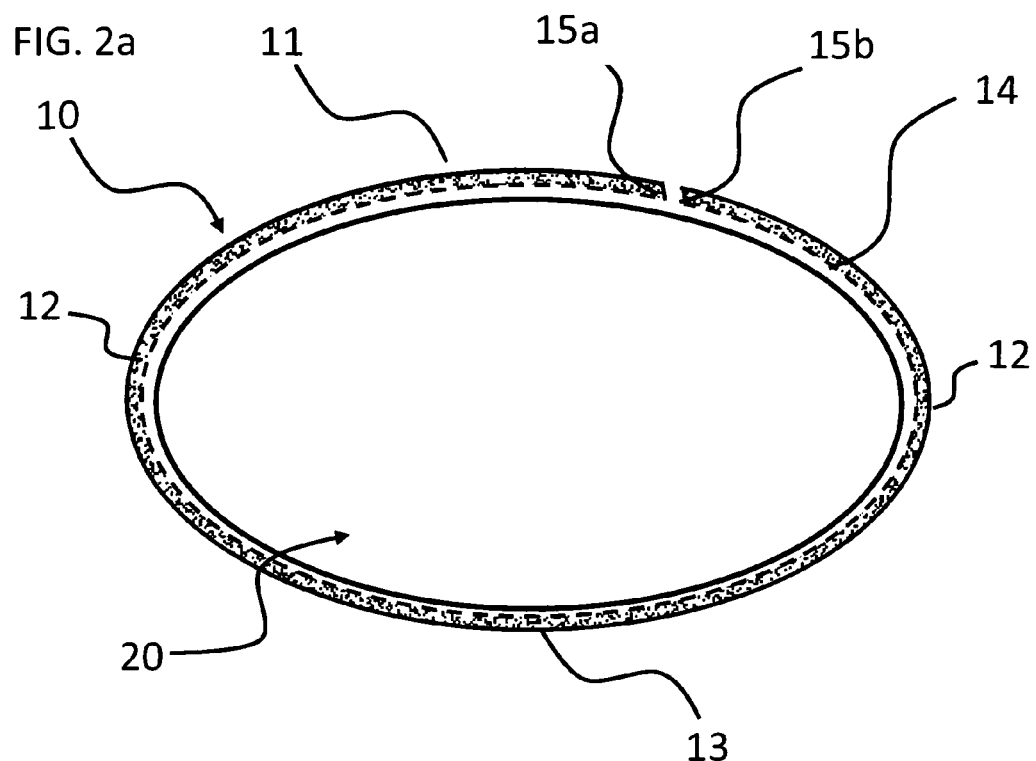
FIG. 2a illustrates a cross-sectional view taken along X-X of FIG. 1c, showing an embodiment of elongated slit.
Figure 2B:
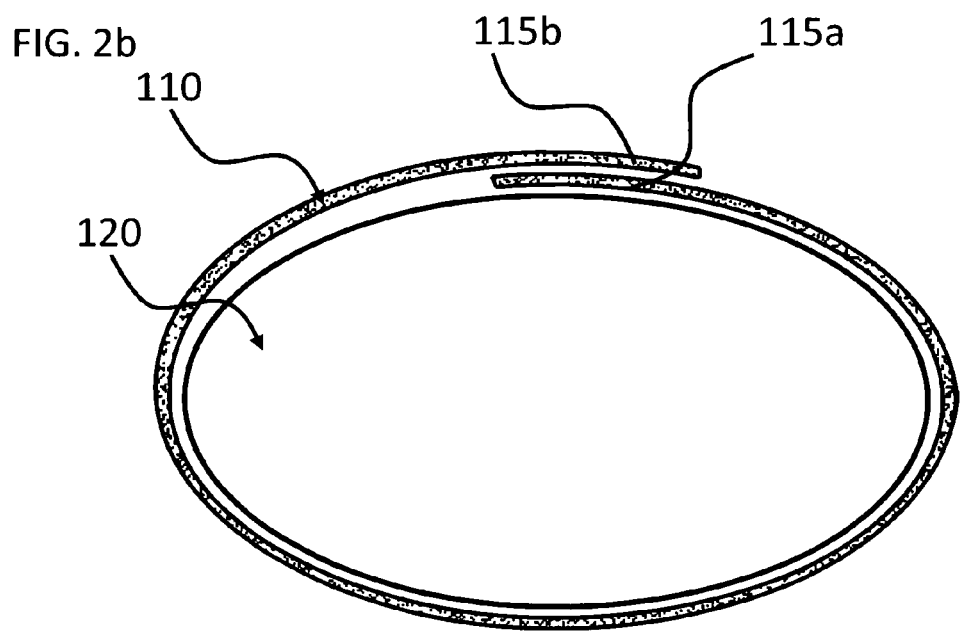
FIG. 2b illustrates a cross-sectional view taken along X-X of FIG. 1c, showing another embodiment of elongated slit wherein the slit is provided with an overlapping portion.

FIGS. 2a and 2b illustrates cross-sectional views taken along X-X of FIG. 1c, showing embodiments of the elongated slit 15. FIG. 1a shows edible chew pill jacket 10 with elongated slit 15 as a flexible slit having edges 15a and 15b that abut to substantially encapsulate pill 20. FIG. 1b shows another embodiment of an edible chew pill jacket 100 with an elongated slit 115 provided as a flexible slit having an inner edge 115a and an overlapping outer edge/portion 115b to completely encapsulate pill 120. In operation, the pill is inserted through flexible elongated slit 15, 115 with the edges 15a, 15b and 115a and 115b. Overlapping outer edge/portion 115b facilitates in completely covering the inserted pill 120 to avoid any direct contact with the recipients tongue.

Vitamin and/nutritional supplements may be used to compose the chew pill jacket to provide enhanced benefits to the animal, pet or human consuming the pill jacket. In another embodiment the chew pill jacket's edible body is composed of at least one joint preserving/joint rebuilding component. Optionally, the chew pill jacket may be composed of a nutritious pet supplement adapted to properly balance metabolic needs that match the joint building ingredients with vitamin and trace mineral content of the formulation. The joint building ingredient chicken collagen type II is selected to have a small molecular chain with a molecular weight in the range of 5,500 to 10,000. Another joint building ingredient, glucosamine sufate for example, needs a substantial quantity of ascorbic acid or vitamin C. However, the vitamin C of the composition is exhausted by the oxidation process of the glucosamine sulfate. More vitamin C is needed for the general upkeep of the pet. Trace copper is needed for cross-linking cartilage tissue and is provided in the mineral content in biologically usable form as chelates. The anti-oxidants provided prevent free radical damage, a key factor in preserving joints.

Generally stated, the pet supplement is provided in a single composition that is a completely mixed, whereby each of the co-factors is made available to the pet's biological tissue at the same time, allowing complete absorption of the nutritional formula. The formula comprises joint building components, vitamin components, mineral components, and anti-oxidant herbal components. Providing proper dosage of this nutritional formulation to a pet based on its weight is extremely important. The formulation shown below is designed for an animal weighing 35 kilograms and has the following active ingredients.

| Joint preserving/building components | |
|---|---|
| Chicken collagen (as collagen type II) | 500-1800 mg |
| Glucosamine hydrochloride | 500-3500 mg |
| Chondroitin sulfate | 500-1500 mg |
| Vitamin components | |
| Vitamin C (as ascorbic acid) | 100-1500 mg |
| Vitamin D (as cholecalciforal) | 100-400 IU |
| Vitamin K (as phylloquinone) | 10-40 mcg |
| Mineral components | |
| Calcium (as calcium carbonate, calcium citrate, malate glycinate) | 400-600 mg |
| Magnesium (as Magnesium oxide magnesium glycinate) | 300-500 mg |
| Zinc (as zinc glycinate) | 10-20 mg |
| Copper (as copper glycinate) | 1-4 mg |
| Manganese (as manganese glycinate) | 3-8 mg |
| Boron (from Boron chelate) | 1-3 mg |
| Herbal cofactor blend | 300-1000 mg | comprising citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as microcrystalline cellulose, croscamellose sodium, silica, magnesium stearate, pharmaceutical glaze and other ingredients that improve processability of the composition and the texture of the final product.

The preferred composition is set forth below.

| Joint preserving/building components | |
|---|---|
| Chicken collagen (as collagen type II) | 800 mg |
| Glucosamine hydrochloride | 1500 mg |
| Chondroitin sulfate | 1200 mg |
| Vitamin components | |
| Vitamin C (as ascorbic acid) | 100 mg |
| Vitamin D (as cholecalciforal) | 200 IU |
| Vitamin K (as phylloquinone) | 20 mcg |
| Mineral components | |
| Calcium (as calcium carbonate, calcium citrate, malate glycinate) | 500 mg |
| Magnesium (as Magnesium oxide magnesium glycinate) | 400 mg |
| Zinc (as zinc glycinate) | 15 mg |
| Copper (as copper glycinate) | 2 mg |
| Manganese (as manganese glycinate) | 5 mg |
| Boron (from Boron chelate) | 1.5 mg |
| Herbal cofactor blend | 500 mg |

Including citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as carob, gum, fruit, microcrystalline cellulose, croscamellose sodium, silica, magnesium stearate, pharmaceutical glaze and other ingredients that improve processability of the composition and the texture of the final product.

The formulation has a pleasant flavor due to chicken products and is immediately consumed by pets as it is chewed, while optimally delivering the pill/tablet appointed to be administered to the animal. The formulation may also have additional flavor enhancers and taste enhancers for the pet.

Having thus described the invention in rather full detail, it will be understood that such detail need not be strictly adhered to, but that additional changes and modifications may suggest themselves to one skilled in the art. For example, the chew pill jacket 10 can be composed of a flavorful, sugar-free substance such as Splenda®, Equal®, Nutra-Sweet®, Sweet N Low® or the like. Fructose can be used as a component of the chew pill jacket 10 to provide a more natural flavor ingredient. These and other changes are intended to fall within the scope of the invention as defined by the subjoined claims.

What is claimed is:

1. An edible chew pill jacket, comprising:
   a. a flexible top wall, side walls and bottom wall configured to form a chamber appointed to receive a pill;
   b. a flexible longitudinal slit integrated within said top wall for providing access to said chamber for insertion of said pill within said edible chew pill jacket, said slit having an inner edge and an overlapping outer edge;
   c. said edible chew pill jacket being composed of at least one flavoring to provide a tasty treat appointed to mask said pill;
   d. said edible chew pill jacket being composed of at least one nutrient or vitamin supplement;
   e. said chew pill jacket having a substantially round, oval or capsule shape; and being capable of substantially encapsulating said pill;
   f. said chew pill jacket includes a textured outer surface for stimulating gums of an animal during chewing;
   h. said chew pill jacket being appointed to house only a single pill;
   i. said chew pill jacket having a substantially round or oval shape adapted to house a capsule or spherical shaped pill or tablet.

2. An edible chew pill jacket as recited by claim 1 composed of at least one joint preserving/joint rebuilding component.

3. An edible chew pill jacket as recited by claim 1, wherein said chew pill jacket is appointed for delivery of said pill to a person.

4. An edible chew pill jacket as recited by claim 1 composed of carob components.

5. An edible chew pill jacket as recited by claim 1 composed of an arabic gum base.

6. An edible chew pill jacket as recited by claim 1, wherein said chew pill jacket has a round shape and diameter ranging from 0.635 cm (0.25 inches) to 2.54 cm (1 inches).

7. An edible chew pill jacket as recited by claim 1, wherein said chew pill jacket is composed of a fruit component.

8. An edible chew pill jacket as recited by claim 1, wherein said chew pill jacket is composed of a jerky.

9. An edible chew pill jacket as recited by claim 1, wherein said chew pill jacket is composed of a chew confection or candy.

10. An edible chew pill jacket as recited by claim 1, wherein said chew pill jacket is appointed for delivery of said pill to a pet, equine or livestock.

* * * * *